(12) United States Patent
Feriani et al.

(10) Patent No.: US 9,550,070 B2
(45) Date of Patent: Jan. 24, 2017

(54) LIGHT PEN DISPENSER

(71) Applicant: Aptar France S.A.S., Le Neubourg (FR)

(72) Inventors: Amir Feriani, Auvernier (CH); Cédric Zaugg, Neuchâtel (CH); Luciano Cravero, Cressier (CH); Frédéric Duquet, Crespières (FR)

(73) Assignee: Aptar France S.A.S., Le Neubourg (FR)

( * ) Notice: Subject to any disclaimer, the term of this patent is extended or adjusted under 35 U.S.C. 154(b) by 795 days.

(21) Appl. No.: 13/919,502

(22) Filed: Jun. 17, 2013

(65) Prior Publication Data

US 2014/0005590 A1 Jan. 2, 2014

(30) Foreign Application Priority Data

Jun. 15, 2012 (EP) ..................................... 12172220

(51) Int. Cl.
*A61N 1/30* (2006.01)
*A61N 5/06* (2006.01)

(52) U.S. Cl.
CPC ..... *A61N 5/0616* (2013.01); *A61N 2005/0644* (2013.01); *A61N 2005/0651* (2013.01)

(58) Field of Classification Search
CPC .. A46B 15/0036; A61N 5/0616; A61B 18/203
USPC .............................................. 604/21; 607/90
See application file for complete search history.

(56) References Cited

U.S. PATENT DOCUMENTS

| | | | |
|---|---|---|---|
| 6,238,424 B1 | 5/2001 | Thiberg | |
| 2007/0185553 A1* | 8/2007 | Kennedy | A61N 5/0616 607/100 |
| 2007/0198004 A1* | 8/2007 | Altshuler | A46B 15/0036 606/9 |
| 2008/0296346 A1* | 12/2008 | Shelton, IV | A61B 17/07207 227/180.1 |
| 2009/0088822 A1* | 4/2009 | Pruitt | A61N 5/0616 607/89 |
| 2011/0224598 A1 | 9/2011 | Barolet | |

FOREIGN PATENT DOCUMENTS

| | | |
|---|---|---|
| DE | 3134953 A1 | 3/1983 |
| DE | 20 2005 013 960 U1 | 4/2006 |
| EP | 1140288 A1 | 10/2001 |
| WO | 91/18646 A1 | 12/1991 |
| WO | 00/41767 A1 | 7/2000 |
| WO | 2012/106678 A1 | 8/2012 |

OTHER PUBLICATIONS

Extended European Search Report issued in corresponding application No. 12172220.1, completed Sep. 25, 2012 and mailed Oct. 8, 2012.

* cited by examiner

*Primary Examiner* — Timothy J Neal
(74) *Attorney, Agent, or Firm* — Griffin & Szipl, P.C.

(57) ABSTRACT

The present invention relates to a portable light pen dispensing device comprising: a housing, an electronics module located in said housing and comprising a light source capable of irradiating skin and stimulating regeneration of the skin to treat skin disorders, a battery for powering the electronics module, wherein the light source comprises one or more LEDs, wherein the electronics module comprises drive means arranged to control the operation of the light source to emit light in a mixed driving mode so as to limit the temperature of the LED while ensuring a sufficient fluency allowing for the skin to be treated.

19 Claims, 8 Drawing Sheets

LIGHT PEN DISPENSER

Figure 1:
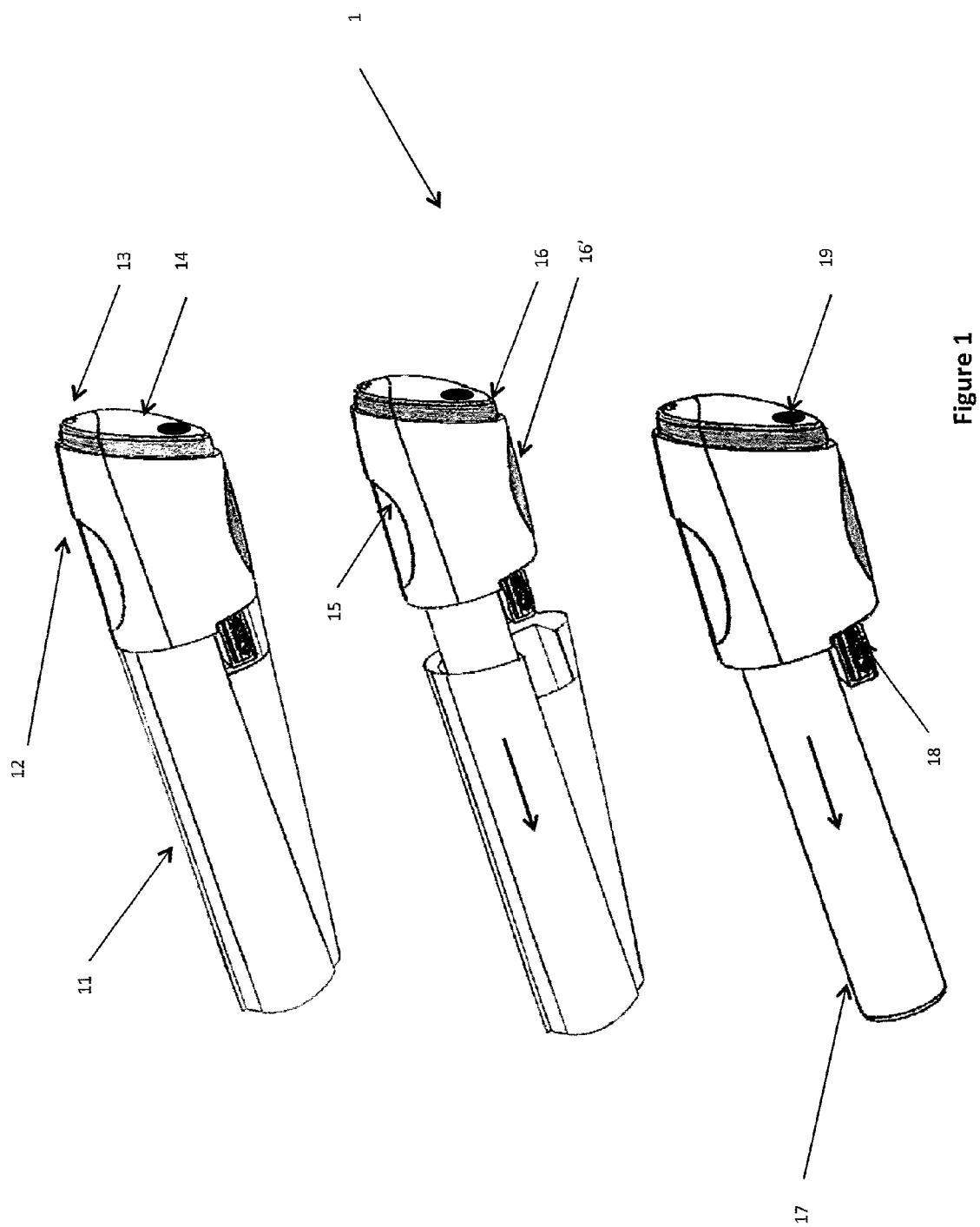

This application claims priority from European Patent Application No. 12172220.1, filed Jun. 15, 2012, the entire disclosure of which is incorporated herein by reference.

FIELD OF THE INVENTION

The present invention concerns a portable light pen dispenser for dispensing irradiating light from LEDs as part of a photodynamic therapy (PDT) for treating skin disorders, and possibly also dispensing media.

BACKGROUND OF THE INVENTION

Photodynamic therapy, PDT, has now reached the level of being an accepted treatment for a number of situations, among which are acne, wrinkles or even several forms of cancer.

Irradiating skin with light stemming from LEDs for treating skin disorders is known, for example to treat acne. The document US 2011/0224598 describes a method of treating inflammatory acne on the skin of a patient, the method comprising irradiating the skin of the patient with radiant infrared light emitting diode (LED) light, subsequently applying the photosensitizing agent 5-aminolevulinic acid (ALA) onto the skin of the patient and irradiating the ALA treated skin with visible LED light. The method described demands high constraint from a patient, as s/he has to undergo an initial 15-minute exposure to light, followed by a 60-minute application of ALA and then a final light exposure of 23 minutes. Such sessions have to be repeated regularly for the therapy to become effective.

It is known that by irradiating skin by emitting light as invisible light in the range of 800 nm to 1100 nm can be used to heal skin diseases. For example, it is known that irradiating the skin with a wavelength of around 835 nm is used for wound healing and around 1070 nm for cold sore surface treatment.

In general, by emitting light of a certain wavelength, for example from 400 to 700 nm, treatment of a skin condition can be performed. LEDs can trigger natural intracellular photo-biochemical reactions. To have any effect on a living biological system, LED-emitted photons must be absorbed by a molecular chromophore or photoacceptor. Light, at appropriate doses and wavelengths, is absorbed by chromophores and other light-absorbing entities within the mitochondria and cell membranes of cells. For example, it is known that by irradiating the skin with a wavelength of around 630 to 660 nm, a stimulation of cell metabolism is caused that activates the generation of collagen in the skin allowing to regenerate the skin, such as reducing wrinkles It is known that a threshold level of power of irradiation must be achieved before such natural process can happen and that the irradiation must take place for a certain duration.

Thus, the time and power of irradiation is important to generate collagen.

Furthermore, the irradiation heats the skin. It is known that too much heat, this uncontrollable level of temperature can have undesirable photo-biochemical reactions or may incur damage to the skin, so that such should be avoided. There are several ways described to limit such heating of the skin.

The document DE 3134953 describes an infrared irradiation device that comprises an infrared light source that is designed as an infrared laser and whose light is directed at the area of skin to be treated medically/therapeutically. The infrared laser is controlled by a control circuit and emits coherent infrared pulse signals at a frequency of 0.1 Hz to 5 kHz, preferably 8 to 50 Hz. The frequency can be adjusted by means of an adjustment member as a function of the skin temperature, that can be measured by means of a temperature sensor and can be displayed in an optical display arrangement. The output of the infrared laser is low, so that the irradiated area of skin is not appreciably heated. According to this document, the skin should not heat to more than 42° C. to avoid damage.

The document WO 91/18646 discloses a device and method for photothermotherapy effected by pulsed ultraviolet, visible or infrared laser radiation passing through a system that assures the necessary laser pulse fluence to a bio-tissue treatment region. While the pulsed local heating of micro regions in the tissue reaches therapeutic levels a unit measuring the local heating by a single pulse and the average heating by a train of pulses controls, by way of feedback, a control unit that determines the pulse energy and repetition period and the total exposure dose to provide a required therapeutic effect without risk of thermal damage to the exposed tissue region.

The document U.S. Pat. No. 6,238,424 discloses an apparatus for external medical treatment with light. A light-emitting device is provided that is adapted to be held in close proximity to the body of an individual and that includes light-emitting diodes or corresponding elements that are adapted to emit monochromatic light of a first wavelength. The light emitting device is driven by a drive arrangement for causing the light-emitting device to emit the monochromatic light over a first predetermined time period in a first state, and thereafter emit selectively monochromatic light of a different wavelength than the first wavelength and over a second predetermined time period in a possible second state. The drive arrangement causes the light-emitting device to pulsate the emitted light in accordance with a predetermined pulse frequency or series of pulse frequencies over the respective time periods, and causes the light-emitting device to emit the pulsating light with a pulse length that lies within an interval of about 60% to about 90% of the time between respective start edges of two mutually sequential pulses.

The document EP 1140288 discloses an apparatus for external medical treatment administered with the aid of light. The apparatus includes a light-emitting device that is intended to be held against or in the close proximity of the patient's body, and means for driving the light-emitting device, wherein the light-emitting device includes light-emitting diodes or corresponding elements adapted to emit monochromatic light, wherein the drive means is adapted to cause the light-emitting device to emit one or more types of monochromatic light over one or more predetermined time periods and to pulsate the light emitted in accordance with a predetermined pulse frequency or series of pulse frequencies over said time periods, wherein said drive means includes a computer and circuits for driving the light-emitting diodes, wherein the computer includes input means for inputting data relating to an intended treatment, wherein the computer is adapted to deliver electric signals to the drive circuits, wherewith intended light-emitting diodes function to emit light within predetermined time periods and at predetermined pulse repetition frequencies. The invention is characterised in that at least the drive circuits of the drive means are mounted in the light-emitting device.

Although such devices may avoid overheating of the skin, they are complicated and often require a separate computer for controlling the operation thereof. Moreover, some of said devices require a skin temperature sensor.

The present invention addresses these problems in a handheld and battery-operated light pen dispenser as defined in the appended claims.

SUMMARY OF THE INVENTION

This light pen dispensing device allows efficient operation of the light sources while preventing overheating of the skin in a simple manner and can be programmed for different skin disorders and may be used in conjunction with different topical ointments.

In accordance with a first embodiment of the invention, a portable temperature-sensorless light pen dispensing device (1) is provided comprising: a housing (11, 12), an electronics module (2) located in said housing (11, 12) and comprising a light source (23) capable of irradiating skin and stimulating regeneration of the skin to treat skin disorders, and a battery (22) for powering the electronics module (2), wherein the light source comprises one or more LEDs, wherein the electronics module (2) comprises drive means (26) arranged to control the operation of the light source (23) to emit light in a mixed driving mode so as to limit the temperature of the LED (23) without a temperature sensor while ensuring a sufficient fluency allowing for the skin to be treated.

Other details and different variants of the invention are defined in the dependent claims.

For example, in accordance with a second embodiment of the present invention, the first embodiment is modified so that said driving means (26) is arranged to drive the light source in a continuous-wave driving mode and a pulsed-wave driving mode, and wherein said driving means is arranged to change the driving mode as a function of time. In accordance with a third embodiment of the present invention, the first embodiment or the second embodiment is modified so that said housing (12) comprises a detachable electronics module (2) comprising the light source (23) allowing for exchanging the electronics module according to a desired skin disorder treatment. In accordance with a fourth embodiment of the present invention, the first embodiment, the second embodiment, or the third embodiment is modified so that said light source emits light at a wavelength of around 400 to around 1100 nm.

In accordance with a fifth embodiment of the present invention, the first embodiment is modified so that said housing consists of a first section (11) and a second section (12), where the first section and the second section are detachably fixed to each other. In accordance with a sixth embodiment of the present invention, the first embodiment, the second embodiment, the third embodiment, the fourth embodiment or the fifth embodiment is modified so that said second section (12) comprises said light source (23) and wherein said second section (12) has a surface section (14) that is transparent to the light emitted from the light source (23) so as to allow for dispensing of the light onto skin to be treated. In accordance with a seventh embodiment of the present invention, the first embodiment, the second embodiment, the third embodiment, the fourth embodiment, the fifth embodiment or the sixth embodiment is modified so that it further comprises an on/off switch (25) for activating the electronics module (2).

In accordance with an eighth embodiment of the present invention, the first embodiment, the second embodiment, the third embodiment, the fourth embodiment, the fifth embodiment, the sixth embodiment or the seventh embodiment is modified so that it further comprises a skin detector switch (16, 16') for activating the light source (23) only when the skin detector switch (16, 16') is on contact with the skin. In accordance with a ninth embodiment of the present invention, the first embodiment, the second embodiment, the third embodiment, the fourth embodiment, the fifth embodiment, the sixth embodiment, the seventh embodiment or the eighth embodiment is modified so that it further comprises a fluid dispenser (17, 13) for dispensing fluid. In accordance with a tenth embodiment, the ninth embodiment is modified so that said fluid dispenser is arranged substantially parallel to said transparent light surface section (14) to dispense fluid substantially at the same skin surface area that is irradiated by said light source (23). In accordance with an eleventh embodiment, the ninth embodiment or the tenth embodiment is modified so that said fluid dispenser comprises a disposable cartridge (17) arranged to contain fluid. In accordance with a twelfth embodiment, the ninth embodiment, the tenth embodiment or the eleventh embodiment is modified so that it further comprises a pump actuator (15) for activating pumping of fluid from said fluid dispenser to exit said light pen dispenser.

In accordance with a thirteenth embodiment, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment or the twelfth embodiment is modified so that it further comprises a power management module (28) for verifying the level of said battery (22). In accordance with a fourteenth embodiment, the thirteenth embodiment is modified so that it further comprises a battery level indicator (29) controlled by said power management module (28). In accordance with a fifteenth embodiment, the thirteenth embodiment or the fourteenth embodiment is modified so that the electronic module is arranged to change the intensity of said light source as a function of the detected battery level to indicate an End-Of-life state of said battery.

In accordance with a sixteenth embodiment, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, or the fifteenth embodiment is modified so that it further comprises a communication module (18) connected to said electronics module (2) and arranged to communicate with an external device. In accordance with a seventeenth embodiment, the sixteenth embodiment is modified so that said communication module is a USB connector. In accordance with an eighteenth embodiment, the sixteenth embodiment is modified so that said communication module is a wireless module.

In accordance with a nineteenth embodiment, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, the sixteenth embodiment, the seventeenth embodiment or the eighteenth embodiment is modified so that it further comprises a diagnostic skin sensor (19) arranged on the housing (12).

In accordance with a twentieth embodiment, a method is provided for use of a portable temperature-sensorless light pen dispensing device (1) according to anyone of the preceding claims for controlling the operation of the light source (23) to emit light in a mixed driving mode so as to limit the temperature of the LED (23) without a temperature sensor that includes the steps of irradiating the skin of a user exposed to the light pen dispensing device with light emitting from the one or more LEDS, driving the electronics module in a mixed driving mode during the irradiating to emit light in a mixed driving mode so as to limit the temperature of the LED (23) without a temperature sensor while ensuring a sufficient fluency allowing for the skin to be treated.

BRIEF DESCRIPTION OF THE INVENTION

Figure 2:
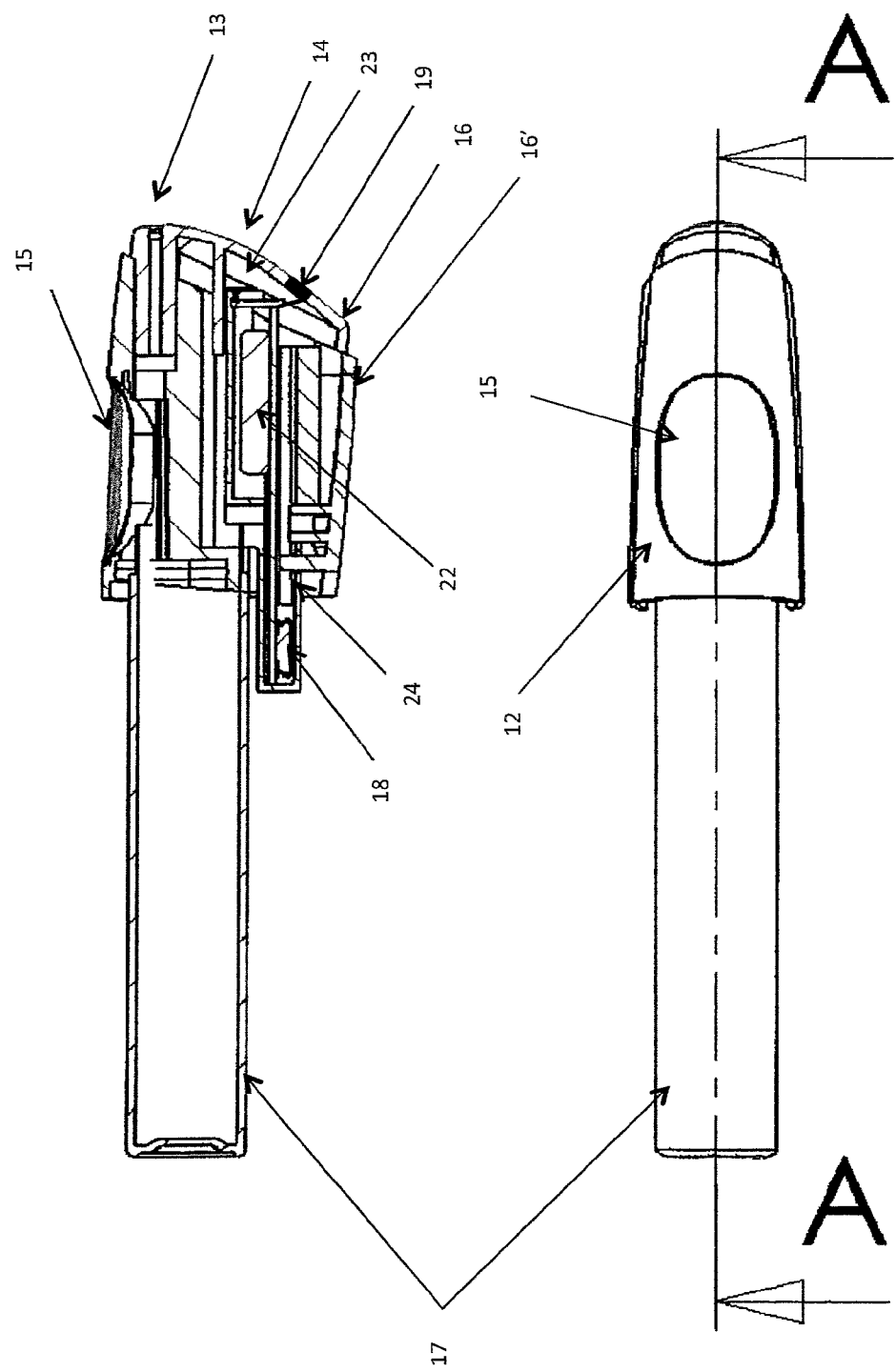
Figure 3:
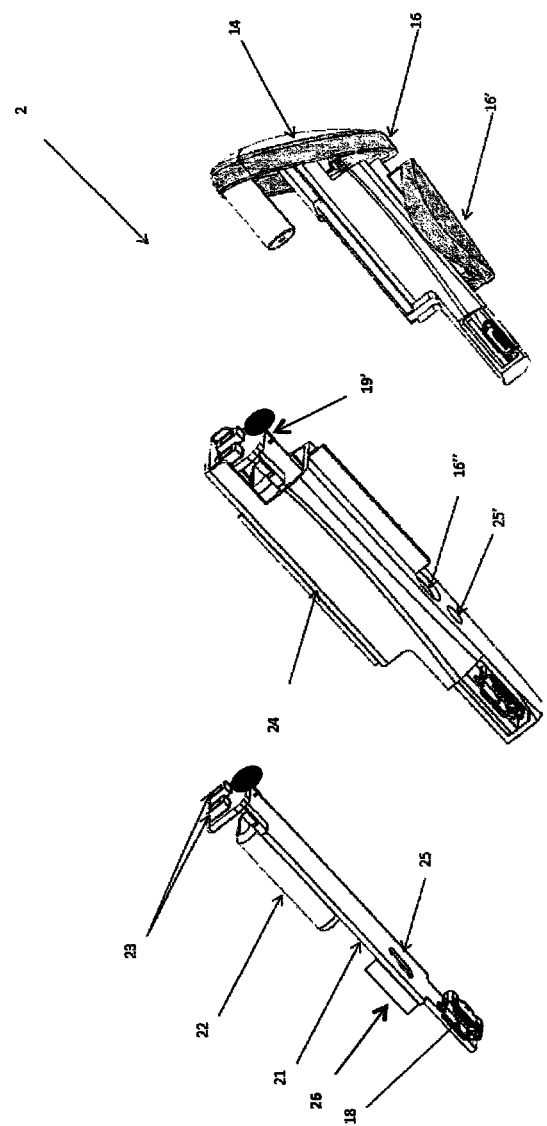
Figure 4:
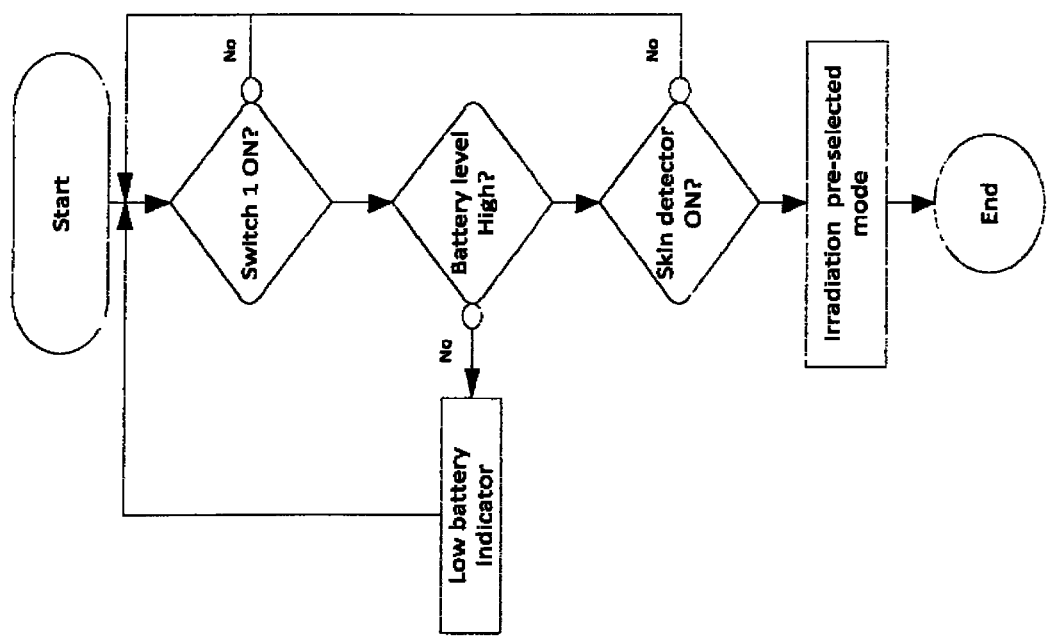
Figure 5:
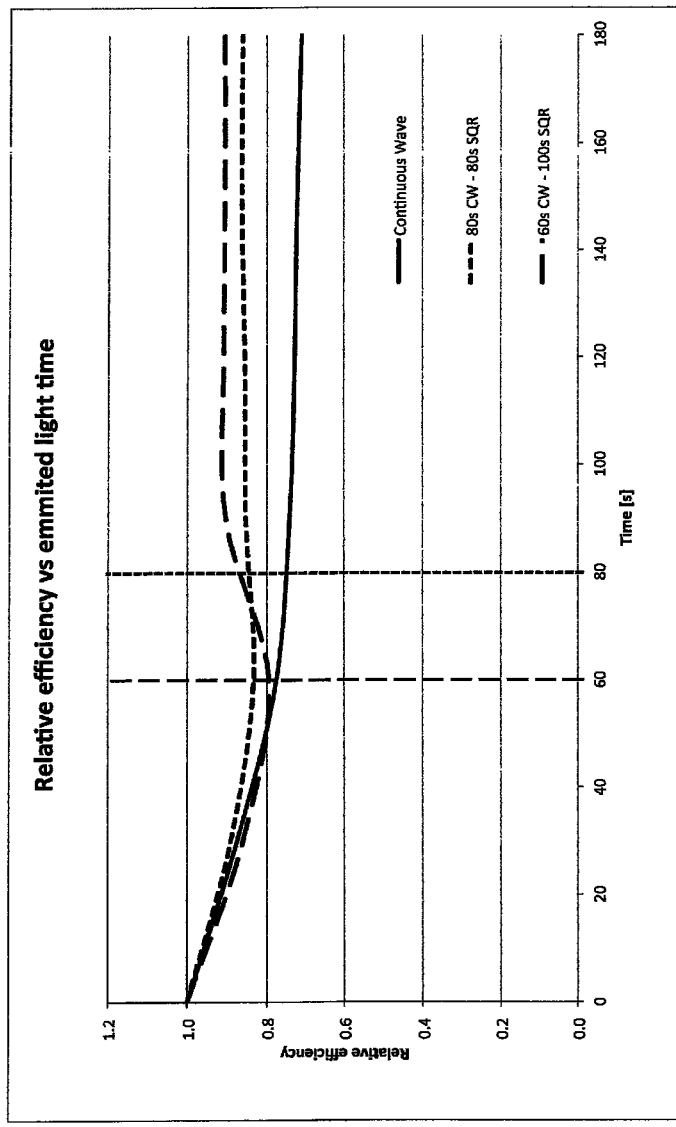
Figure 6:
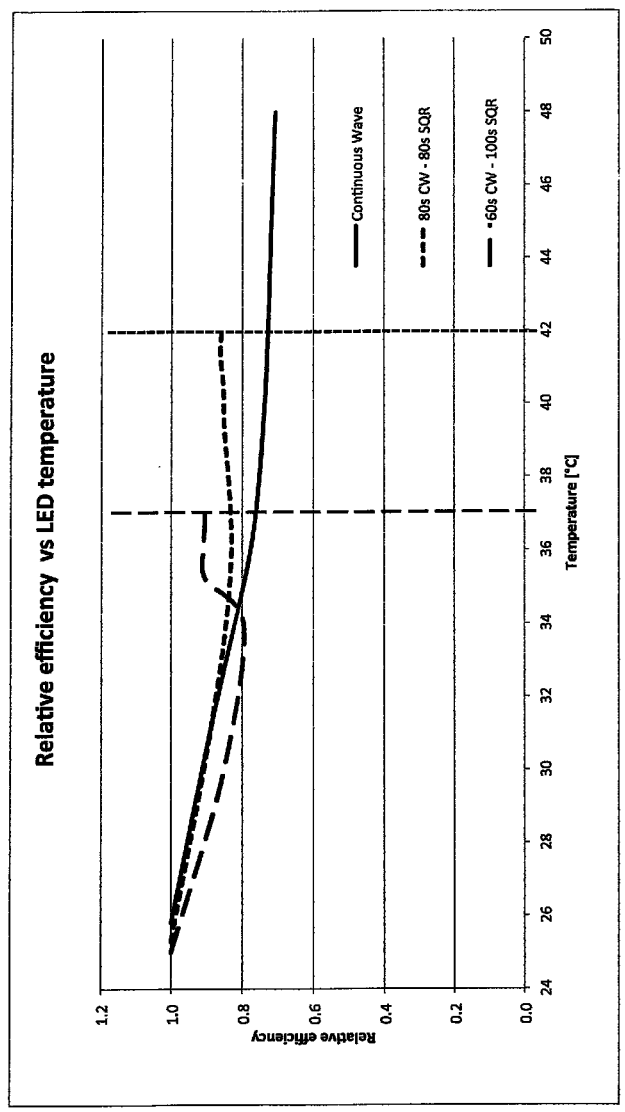
Figure 7:
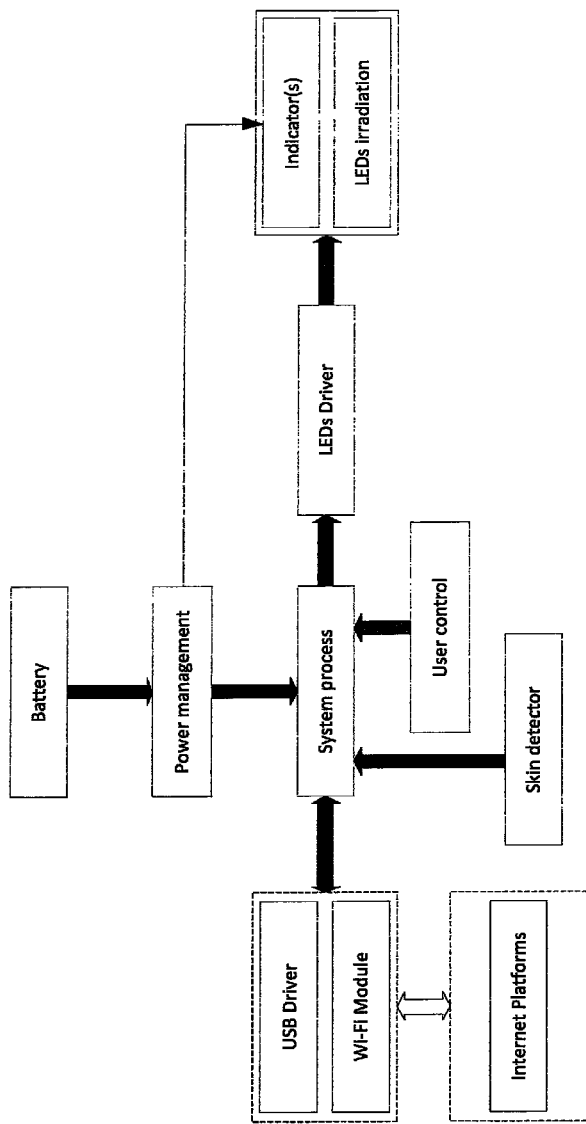
Figure 8:
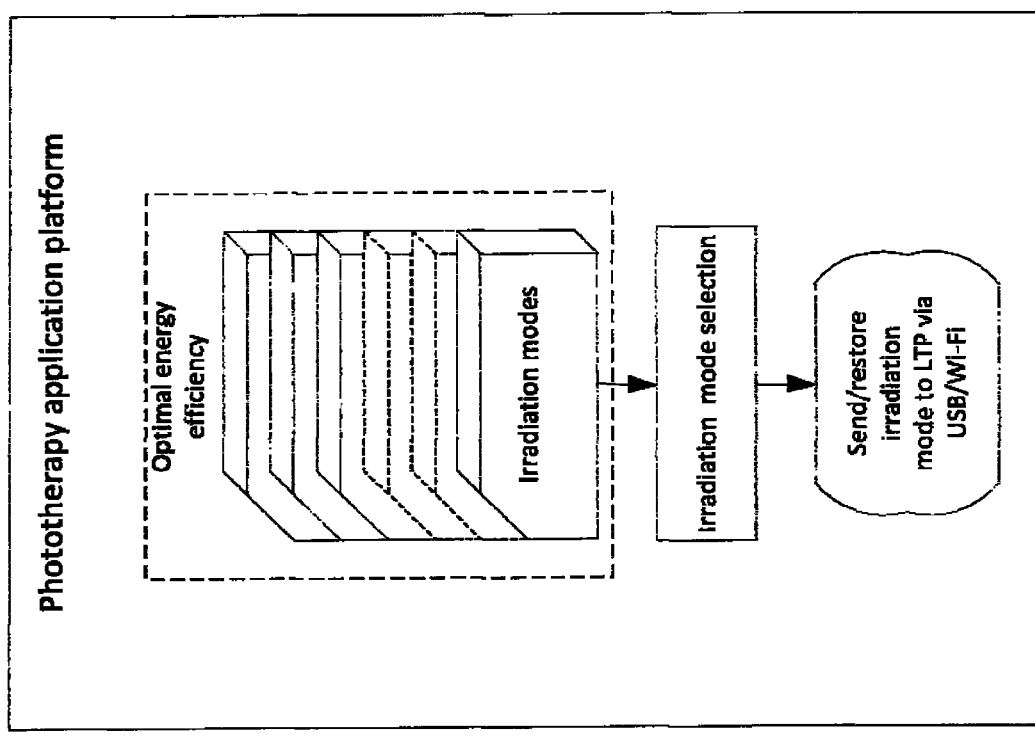

The invention will be better understood with the help of the following detailed description and the accompanying drawings illustrating possible embodiments of the invention:

FIG. 1 shows a general overview of a light pen dispenser according to the present invention, FIG. 2 shows a cross-section of the light pen dispenser of FIG. 1, FIG. 3 shows in more details the electronics module of the light pen dispenser according to the present invention, FIG. 4 shows a flow chart of an operation of the light pen dispenser according to the present invention, FIG. 5 shows a graph representing the relative efficiency of a LED with respect to the duration of emitted light, FIG. 6 shows a graph representing the relative efficiency of a LED with respect to the LED temperature, FIG. 7 shows a block diagram of the functional elements of the electronics module of the light pen dispenser according to the present invention, and FIG. 8 shows in more detail a block diagram of a bespoke light irradiation platform shown in the block diagram of FIG. 7.

DETAILED DESCRIPTION OF THE INVENTION

A preferred embodiment of the light pen dispenser according to the present invention will now be described with reference to the Figures.

FIG. 1 shows a light pen dispenser 1 having a general housing having a first section called applicator body 11 and a second section called dispensing applicator body 12. Applicator body 11 contains a refill 17 that may be a refillable cartridge for containing a fluid to be dispensed. Such fluid may be a cream, an ointment or the like depending on the skin disorder to be treated. Refill 17 can be fitted onto dispensing applicator body 12 in a manner known as such so that fluid may enter the dispensing applicator body for dispensing thereof.

To this effect, dispensing applicator body 12 may receive at a first extremity the refill and is provided at the other extremity with a nozzle 13 that is a product dispensing hole for dispensing fluid received from refill 17. A pump actuator 15 is further provided on dispensing applicator body 12 allowing a user to apply pressure on fluid to facilitate the dispensing thereof.

At the same extremity of dispensing applicator body 12 that holds the nozzle 13 a light guide applicator 14 is provided. Light guide applicator 14 allows light emitted from a light source such as one or more light emitting diodes (LED) contained within the light pen dispenser to exit the dispenser, as will be described in more detail hereafter.

Switch detectors 16 and 16' may be further provided to control operation of the light pen dispenser.

Advantageously, a communication module, in this example a USB connector 18 may be provided for communication with an external device, as will also be explained hereafter. Other types of communication modules may of course be used instead or even a wireless module such as Bluetooth® or Wi-Fi may be used.

FIG. 2 shows in more detail dispensing applicator body 12 by way of a cross-sectional view. As can be seen, refill 17 is in fluidic contact with product dispensing hole, or nozzle 13 so as to allow fluid to flow from the refill to outside of the light pen dispenser, onto skin of a user through activation of pump actuator 15.

A light source 23, in this example one or more LEDs, may be provided in close proximity to light guide applicator 14 for emitting light from the light pen dispenser to skin of a user.

Light may be emitted at a wavelength from around 400 nm to 700 nm, and preferably at around 660 nm, depending on the skin order to be treated. By irradiating the skin with a wavelength of around 660 nm, a stimulation of cell metabolism is caused that activates the generation of collagen in the skin allowing to regenerate the skin. Thus light guide applicator 14 is a section of dispensing applicator body 12 that is transparent to the wavelength of light emitted from the light source. A battery 22, for example a LiPo rechargeable battery, is provided for powering the light source, i.e. LED 23, and electronics related to the control and operation of the LED. Such electronics include drive means 26, see FIG. 7, for driving the light source in, for example a continuous-wave mode and a pulsed mode. To this effect, an electronic module 2 is provided with the USB connector 18 and to LED 23 in dispensing applicator body 12 allowing control of the operation of LED 23.

FIG. 3 shows in more detail electronic module 2 comprising USB connector 18, battery 22, LED(s) 23, a PCB 21 for holding the electronic components such as the LED drive means 26 and the LED(s) and an on/off push button 25 for activating and deactivating the electronic module 2. A diagnostic skin sensor 19 may further be provided. Electronic module body 24 covers the electronic elements of electronic module 2 and is provided with an access hole 25' allowing to manipulate push button 25 and to connect it to the electronic module as well as with an access hole 16" allowing for connection of switch detector 16' to electronic module 2.

A connection 19' may further be provided allowing for connection of diagnostic skin sensor 19 to the electronics module. This skin sensor is used for analysing, for example, the dryness/humidity of the skin to be treated, or the thickness of the epidermis, the deepness of a wrinkle or the like so as to optimize the treatment of the skin disorder by adapting the power and/or the dispensing of fluid as a result of the analysis.

By pressing the on/off button 25, a user holding the light pen dispenser in his/her hand will activate the electronic module thus allowing for operation of the light pen dispenser. The light pen dispenser typically has an elongated pen-like shape and is formed such that when holding the dispenser in his/her hand, the user will position a first finger, typically the index finger, on pump actuator 15 for allowing activation of possible dispensing of fluid and a second finger, typically the thumb, on switch detector 16'.

When the light pen dispenser is positioned on a skin surface to be treated, such as a cheek or the surface under an eye, switch detector 16 will enter into contact with the skin of the surface to be treated. Switch detectors 16 and 16' are configured to operate in combination to allow for activation of the light source, i.e. of LED 23. Such operation of detection switches may be performed by using as the switch detectors 16, 16' metal film conductors applied to the dispensing applicator body 12 causing a simple short-circuit by way of the passage of a current through the skin to be treated in contact with switch detector 16 and the finger in contact with switch detector 16'. Such means are well known as such. These means are used here as a safety measure to avoid undesirable operation of the light source. In fact, the LEDs should not illuminate when the light pen is not in contact with the skin in order to avoid light irradiating to unwanted places such as the eyes of the user. Also, it may prevent any unwanted use when a child is playing with the light pen dispenser. Thus, once on/off push button 25 is activated, the light pen dispenser may be operated.

Any fluid contained in the refill cartridge 17 may be dispensed by activating pump actuator 15 thus allowing fluid to flow from refill 17 out of the dispenser by way of product dispensing hole 13.

If switches 16 and 16' are also activated, it is possible to irradiate the skin by emitting light from the LEDs 23. This could be done at the same time as the dispensing of fluid, or light could be emitted separately thereof, either before dispensing any fluid or thereafter depending on the skin condition that is to be treated.

Preferably, the fluid dispensing hole 13 is arranged substantially parallel to the light guide applicator 14 in order to dispense fluid substantially at the same skin surface area that is irradiated by the light source 23.

Advantageously, electronics module 2 can be conceived as a separate module that can be fitted and detached from the housing of light pen dispenser 1. This allows for easy exchange of the electronics module and the LEDs depending on the skin order to be treated. For example, LEDs of a different wavelength (colour) are required for different skin treatments.

FIG. 4 shows a flow chart of an operation process of the light pen dispenser according to the present invention. First of all, the process starts by checking whether on/off button 25 is turned on or not, as shown by the step "switch 1 on?". If the push button is not on, the light pen dispenser is not operable and the process returns to the initial start position. If the push button 25 is turned on, the battery level of the dispenser may be checked. To this effect, advantageously, the electronics module 2 of the light pen dispenser may be provided with a power management module 28, see FIG. 7, comprising a battery voltage level detector that ensures correct operation as long as the battery level is above a certain threshold limit that allows for activation of all electronic elements in electronic module 2. If the level is not high enough, a low battery indicator 29, see FIG. 7, may be activated to provide this information to a user. It is also possible to use the LEDs 23 at a very low power irradiation as a low battery indicator when the used LEDs 23 is (are) are in the visible light wavelength domain. This may be realised in a way known as such to a person in the art so that it is not further explained here.

Alternatively, if the battery level is detected as being low, the light source 23 may be activated with a reduced intensity or with a specific flashing operation to indicate an End-Of-Life state of the battery so that a user may be aware of the necessity to charge or to change the battery.

If the battery level is sufficiently high, the next step is to check whether the skin detector is on or not. The skin detector turns on when both switch detector 16 and 16' make contact with skin, as explained above. If the skin detector is off, the process stops and returns to the initial start position.

If the skin detector is on, then the LED or LEDs may be activated. The activation of the LEDs can be carried out according to a pre-selected mode. One or more modes may be pre-programmed in a memory module forming part of the electronic module. For example, the LED may be activated for a predetermined duration, such as, for example, between 20 to 160 seconds. Furthermore, the LED may be activated to operate continuously or in a pulsed mode, depending on the intended skin condition to be treated.

The duration should be sufficiently long, with sufficient power irradiating from the LED to allow for generation of collagen in the skin, and should be limited in time so that a user will still be inclined to use the dispenser. Experimentation has determined that such duration should be limited to 160 seconds allowing for correct ergonomic use of the device. Naturally, such limitation in duration is a simple design choice that can be changed if desired.

During further experimentation, it has come to the knowledge of the present inventor that the emitting efficiency of a LED changes over time and with temperature. FIG. 5 shows a graph representing the relative efficiency of a LED with respect to the duration of emitted light. As can be seen, the light efficiency is initially 100% (1.0). With time, this efficiency lowers to around 70%. This is probably due to the increase in temperature of the LED. In fact, the present inventor measured the change of efficiency with respect to the temperature of the LED. Once activated, a LED emits light and thus irradiates heat. Although this is generally much less than other light sources, there is a noticeable drop in efficiency due to an increase of temperature of the LED.

FIG. 6 shows a graph representing the relative efficiency of a LED with respect to the LED temperature, as determined during measurements. As shown, for the measured LED, the initial efficiency is 100% (1.0) at a room temperature of about 25° C. As the LED heats up during activation, its surrounding temperature increases and its efficiency lowers to around 70%.

By controlling the drive-operation of the LED, it is thus possible to limit the drop in efficiency. As shown in FIGS. 5 and 6, measurement were carried out by changing the drive of the LED from a continuous wave to a mixture of continuous wave drive mode and pulsed drive mode.

In the shown example, the total drive time was limited to 160 seconds, in line with the above-explained ergonomically accepted duration. By only using a continuous wave (CW), the efficiency decreases over time from 100% to around 70%. In analogy, the LED temperature rises from 25° C. to around 48° C. or more that also results in a loss of efficiency from 100% to around 70%.

By switching the drive from continuous wave to a pulsed wave drive (PW, indicated as SQR for square in the Figures), the loss of efficiency can be controlled to the extent that a minimal efficiency of more than 80% can be obtained. As shown in FIG. 5, in an example the CW drive is changed after 80 seconds to a PW drive thereby allowing to stabilize the efficiency, as it avoids a further drop. In another example, the CW drive is switched after 60 seconds to a PW drive resulting in an increase in efficiency.

As the efficiency increases, the temperature rise is also controlled. FIG. 6 shows that the temperature can be limited to a value by changing the drive operation of the LED.

The switching to a PW drive allows for a temporal cooling of the LED that thus lowers its temperature and increases its efficiency.

According to the present invention, it is thus possible to control the operation of the LED to avoid a drop in efficiency of the LED over time that will then result in a control of the temperature.

As mentioned above, it is known that irradiation of a light source that causes heating of the skin over 37° C. may result in undesirable and uncontrollable photo-biochemical reactions of the skin or may result in skin damage when the temperature is over 42° C. Thanks to the present invention, it is possible to control the operation of the LED, i.e. by switching from CW-mode to PW mode, so that the efficiency of the LED can be stabilized and its temperature can be controlled while ensuring a sufficient fluency allowing for the skin to be treated. Furthermore, this also leads to reduced power consumption, as the PW mode uses less energy, so that a higher efficiency may be achieved.

This allows programming the electronics module 2 by defining a specific drive mode of the LED for a specific application of light treatment. As shown in FIG. 6, the total duration may be limited to 160 seconds and the temperature can be limited to 37° C. (60 s CW followed by 100 s PW) or to 42° C. (80 s CW followed by 80 s PW) depending on the drive mode of the LED. Naturally, several drive modes can be pre-programmed allowing selection of a specific operation.

Such selection may be carried out by a user, but preferably, it may be defined as a function of the fluid that is to be applied. For example, if a fluid is used for anti-wrinkle treatment, a different temperature may be desirable when compared to the use of a fluid for the treatment of acne.

Thus, the light pen dispenser according to the present invention can be programmed that the electronics module controls the operation of the LED so as not to exceed, for example, 37° C. by triggering a suitable operation of the light source drive means 26.

It thus is possible to program the driving mode in such a manner that the LEDs remain below a certain temperature. By doing so, the efficiency of the LED will not drop below a certain threshold thus ensuring sufficient power to obtain the desired effect in the treatment of a skin disorder.

Furthermore, for a light pen dispenser, the LED to be used can be measured and calibrated such that the driving modes can be programmed as a function of time to ensure the desired operation. As such, overheating of the LED can be avoided without requiring any temperature sensor or with any heat-dissipating unit, as for example cooling liquid or a temperature sink. Thus, a portable temperature-sensorless light pen dispensing device may be obtained.

FIG. 7 shows a block diagram of the functional elements of the electronics module 2 of the light pen dispenser according to the present invention. The functional elements of the electronics module 2 comprise a system processor CPU 27 for controlling the operation. CPU 27 is powered by battery 22, by way of power management module 28, as explained above. Advantageously, power management module 28 is connected to a battery level indicator 29 to indicate whether the battery is low or not, such as for example by a red (low) or green (OK) light. CPU 27 is connected to the LED driving means 26 for suitably driving the light source 23.

A user control is provided for controlling operation of the CPU. Such user control may be on/off push button 25. Also, a skin detector is provided, by way of detectors 16 and 16' explained above, for also controlling the operation of the CPU to prevent untimely activation of the light source.

CPU is further connected with communication module 18 for communication with an external device or network. Such communication module may be arrange to allow programming of the LED driver, but is may also receive information from the CPU. It is further arranged to connect to a network such as the Internet.

FIG. 8 shows in more detail a block diagram of a bespoke light irradiation platform shown in the block diagram of FIG. 7. Such platform may be located on the Internet or on any suitable network that may be connected to the light pen dispenser by way of communications module 18.

This platform allows for feedback to the fluid supplier or to a doctor supervising the skin disorder treatment. As such, it is possible to allow for personalization of the treatment and/or to optimize the treatment itself, for example by changing the pre-programmed driving modes of the light source.

It may further be connected to a suitable platform where users or professionals can share treatment results and parameters used for the treatment and possible even interact by way of requesting new programming of driving modes.

As shown in FIG. 8, it is thus possible to determine an optimal energy efficiency based on several input results from several users, select an optimal mode and adapt the irradiation modes by re-programming the drive means of the light source by way of the communication module 18.

Further, such sharing and interactive activity may take place by the use of a smartphone by using an appropriate application therefore.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A portable temperature-sensorless light dispensing device having an elongated pen-like shape, the light dispensing device comprising:
    (a) a housing;
    (b) an electronics module located in the housing and comprising
        (i) a light source capable of irradiating skin and stimulating regeneration of the skin to treat skin disorders; and
        (ii) drive means disposed to control the operation of the light source; and
    (c) a battery for powering the electronics module;
    wherein the light source comprises one or more LEDs, wherein the drive means controls the operation of the light source to emit light in a mixed driving mode, wherein the driving means is disposed to drive the light source in a continuous-wave driving mode and a pulsed-wave driving mode, and wherein the driving means is disposed to change the driving mode during operation of the LED as a function of time, and wherein the mixed driving mode limits the temperature of the LED without a temperature sensor while ensuring a sufficient fluency allowing for the skin to be treated.

2. A portable temperature-sensorless light dispensing device according to claim 1, wherein the housing comprises a detachable electronics module comprising the light source, wherein the detachable electronics module allows the electronics module to be exchanged according to a desired skin disorder treatment.

3. A portable temperature-sensorless light dispensing device according to claim 1, wherein the light source emits light at a wavelength of approximately 400 nm to approximately 1100 nm.

4. A portable temperature-sensorless light dispensing device according to claim 1, wherein the housing consists of a first section and a second section, wherein the first section and the second section are detachably fixed to each other.

5. A portable temperature-sensorless light dispensing device according to claim 4, wherein the second section comprises the light source and wherein the second section has a surface section that is transparent to the light emitted from the light source, wherein the surface section allows a light from the light source to be dispensed onto skin to be treated.

6. A portable temperature-sensorless light dispensing device according to claim 1, further comprising:
(d) an on/off switch that controls the electronics module.

7. A portable temperature-sensorless light dispensing device according to claim 1, further comprising:
(d) a skin detector switch that activates the light source only when the skin detector switch is in contact with skin.

8. A portable temperature-sensorless light dispensing device according to claim 1, further comprising:
(d) a fluid dispenser that dispenses fluid.

9. A portable temperature-sensorless light dispensing device according to claim 8, wherein the fluid dispenser is disposed substantially parallel to the transparent light surface section to dispense fluid substantially at the same skin surface area that is irradiated by the light source.

10. A portable temperature-sensorless light dispensing device according to claim 8, wherein the fluid dispenser comprises a disposable cartridge able to contain fluid.

11. A portable temperature-sensorless light dispensing device according to claim 8, further comprising:
(e) a pump actuator that activates pumping of fluid from the fluid dispenser to exit the light pen dispenser.

12. A portable temperature-sensorless light dispensing device according to claim 1, further comprising:
(d) a power management module that is able to verify the level of the battery.

13. A portable temperature-sensorless light dispensing device according to claim 12, further comprising:
(e) a battery level indicator controlled by the power management module.

14. A portable temperature-sensorless light dispensing device according to claim 12, wherein the electronic module is arranged to change the intensity of the light source as a function of the detected battery level to indicate an End-Of-life state of the battery.

15. A portable temperature-sensorless light dispensing device according to claim 1, further comprising:
(d) a communication module connected to the electronics module and arranged to communicate with an external device.

16. A portable temperature-sensorless light dispensing device according to claim 15, wherein the communication module is a USB connector.

17. A portable temperature-sensorless light dispensing device according to claim 15, wherein the communication module is a wireless module.

18. A portable temperature-sensorless light dispensing device according to claim 1, further comprising:
(d) a diagnostic skin sensor arranged on the housing.

19. A method for use of a portable temperature-sensorless light dispensing device having an elongated pen-like shape, the light dispensing device for controlling the operation of the light source to emit light in a mixed driving mode so as to limit the temperature of the LED without a temperature sensor, the method comprising the steps of:

(a) providing a portable temperature-sensorless light dispensing device having (a) a housing: (b) an electronics module located in the housing and comprising (i) a light source capable of irradiating skin and stimulating regeneration of the skin to treat skin disorders; and (ii) drive means disposed to control the operation on of the light source and (c) a battery for powering the electronics module; wherein the light source comprises one or more LEDs, wherein the drive means controls the operation of the light source to emit light in a mixed driving mode, wherein the driving means is disposed to drive the light source in a continuous-wave driving mode and a pulsed-wave driving mode, and wherein the driving means is disposed to change the driving mode during operation of the LED as a function of time, and wherein the mixed driving mode limits the temperature of the LED without a temperature sensor while ensuring a sufficient fluency allowing for the skin to be treated:

(b) irradiating the skin of a user exposed to the light dispensing device with light emitting from the one or more LEDS;

(c) driving the electronics module in a mixed driving mode during the irradiating to emit light in a mixed driving mode, wherein the driving means is disposed to drive the light source in a continuous-wave driving mode and a pulsed-wave driving mode, and wherein the driving means is disposed to change the driving mode during operation of the LED as a function of time, and wherein emitting light in the mixed driving mode limits the temperature of the LED without a temperature sensor while ensuring a sufficient fluency allowing skin to be treated.

* * * * *